US007888312B2

(12) United States Patent
Arnberg

(10) Patent No.: US 7,888,312 B2
(45) Date of Patent: Feb. 15, 2011

(54) METHOD OF TREATING PERIODONTAL DISEASES BY ADMINISTERING A THERAPEUTICALLY EFFECTIVE AMOUNT OF GM-CSF

(75) Inventor: Henrik Arnberg, Uppsala (SE)

(73) Assignee: Innoventus Project AB, Uppsala (SE)

( * ) Notice: Subject to any disclaimer, the term of this patent is extended or adjusted under 35 U.S.C. 154(b) by 0 days.

(21) Appl. No.: 10/599,753

(22) PCT Filed: Apr. 8, 2005

(86) PCT No.: PCT/SE2005/000511

§ 371 (c)(1),
(2), (4) Date: Jul. 25, 2007

(87) PCT Pub. No.: WO2005/097065

PCT Pub. Date: Oct. 20, 2005

(65) Prior Publication Data

US 2008/0038222 A1    Feb. 14, 2008

(30) Foreign Application Priority Data

Apr. 8, 2004    (SE) .................................. 0400942-9

(51) Int. Cl.
*A61K 38/00*    (2006.01)
(52) U.S. Cl. .......................... 514/1.1; 530/350; 530/399
(58) Field of Classification Search .................... None
See application file for complete search history.

(56) References Cited

U.S. PATENT DOCUMENTS

| | | | |
|---|---|---|---|
| 4,804,530 A * | 2/1989 | Sampathkumar ............. | 424/53 |
| 4,810,643 A | 3/1989 | Souza | |
| 5,023,082 A | 6/1991 | Friedman et al. | |
| 5,162,111 A * | 11/1992 | Grabstein et al. .......... | 424/85.1 |
| 5,976,523 A * | 11/1999 | Awaya et al. ............... | 424/85.1 |
| 6,660,258 B1 * | 12/2003 | Tovey ......................... | 424/85.2 |
| 6,682,718 B1 | 1/2004 | O'Uchi et al. | |
| 6,689,351 B1 | 2/2004 | Pierce et al. | |
| 2005/0008614 A1 | 1/2005 | Nieland et al. | |
| 2007/0105824 A1 * | 5/2007 | Erickson-Miller et al. | .. 514/150 |

OTHER PUBLICATIONS

Soskolne W. A., Crit. Rev. Oral Biol. Med. 8: 164-174, 1997.*
B. Weston, et al. "Severe Congenital Neutropenia: Clinical Effects and Neutrophil Function During Treatment with Granulocyte Colony-Stimulating Factor" *Journal of Laboratory and Clinical Medicine* vol. 117, No. 4 (1991) pp. 282-290.
J. Gamonal, et al. "Delayed Neutrophil Apoptosis in Chronic Periodontitis Patients" *Journal of Clinical Periodontology* vol. 30 (2003) pp. 616-623.
J. Goultschin, et al. "The Relationship Between Peripheral Levels of Leukocytes and Neutrophils and Periodontal Disease Status in a Patient with Congenital Neutropenia" *Periodontal Disease in Congenital Neutropenia* vol. 71, No. 9 (2000) pp. 1499-1505.
M.K. Seow, et al. "Cohen Syndrome with Neutropenia-Induced Periodontitis Managed with Granulocyte Colony-Stimulating Factor (G-CSF): Case Reports" *American Academy of Pediatric Dentistry* 20:5 (1995) pp. 350-354.
C.P. Hill, et al. "The Structure of Granulocyte-Colony-Stimulating Factor and its Relationship to Other Growth Factor" *PNAS* vol. 90 (Jun. 1993) pp. 5167-5171.
T. Zink, et al. "Structure and Dynamics of the Human Granulocyte Colony-Stimulating Factor Determined by NMR Spectroscopy, Loop Mobility in a Four-Helix-Bundle Protein" *Biochemistry 33*, (1994) pp. 8453-8463.
A.W. Burgess, et al. "Purification and Properties of Bacterially Synthesized Human Granulocyte-Macrophage Colony Stimulating Factor" *Blood* vol. 69, No. 1 (Jan. 1987) pp. 43-51.
Knusli, C. et al., "Polyethylene glycol (PEG) modification of granulocyte-macrophage colony stimulating factor (GM-CSF) enhances neutrophil priming activity but not colony stimulating activity," *British Journal of Haematology*, 82:654-663 (1992).
NCBI report for protein accession No. P04141.1, Jun. 10, 2008.
"Pharmacology: Drug delivery methods," www.eyetee.net, Copyright 1997-2004, 3 pages.
Margolin et al., "Leakage Around Voice Prosthesis in Laryngectomees: Treatment with Local GM-CSF," *Head & Neck*, 2001, 23:1006-1010.
Nashed et al., "Intraneural injection of corticosteroids to treat nerve damage in leprosy: a case report and review of literature," *J. Med. Case Reports*, 2008, 2:381-385.
Wong et al., "Local vs systemic corticosteroids in the treatment of carpal tunnel syndrome," *Neurology*, 2001, 56:1565-1567.
Zhang et al., "Local injection of insulin-zinc stimulates DNA synthesis in skin donor site wound," *Wound Rep. Reg.*, 2007, 15:258-265.
Greenstein, "Nonsurgical Periodontal Therapy in 2000: A Literature Review," *J. Am. Dent. Assoc.*, 2000, 131: 1580-1592.
Loesche, "The Antimicrobial Treatment of Periodontal Disease: Changing the Treatment Paradigm," *Crit. Rev. Oral Biol. Med.*, 1999, 10(3): 245-275.
Soskolne, "Subgingival Delivery of Therapeutic Agents in the Treatment of Periodontal Diseases," *Crit. Rev. Oral Biol. Med.*, 1997, 8(2): 164-174.
Wikipedia webpage, published Sep. 13, 2009, entitled "Route of Administration.".

* cited by examiner

*Primary Examiner* — Robert Landsman
*Assistant Examiner* — Gyan Chandra
(74) *Attorney, Agent, or Firm* — Fish & Richardson P.C.

(57) ABSTRACT

The invention provides a composition for treatment of a localized bacterial infection and bacterial related disease comprising at least one CSF or fragment or derivative thereof. Also provided is the use of at least one colony stimulating factor (CSF) or fragment or derivative thereof having essentially the biological functionality and activity of the CSF for preparing a medicament for the treatment of a localized bacterial infection and bacterial related disease. The CSF is selected from granulocyte colony-stimulating factor (G-CSF), macrophage colony-stimulating factor (M-CSF), granulocyte-macrophage colony-stimulating factor (GM-CSF), and multi-colony stimulating factor. A method of treatment of a mammal suffering from a localized bacterial infection and bacterial related disease is provided. The localized bacterial infection and bacterial related disease may be a periodontal disease or sinusitis.

11 Claims, No Drawings

METHOD OF TREATING PERIODONTAL DISEASES BY ADMINISTERING A THERAPEUTICALLY EFFECTIVE AMOUNT OF GM-CSF

CROSS-REFERENCE TO RELATED APPLICATIONS

This application is a National Stage application under 35 U.S.C. §371 of International Application No. PCT/SE2005/000511 (WO 2005/097065), filed Apr. 8, 2005, which claims the benefit of priority to Swedish Application Serial No. SE 0400942-9, filed Apr. 8, 2004, all of which are incorporated by reference in their entirety herein.

FIELD OF THE INVENTION

The present invention relates to the treatment of localized bacterial infections and bacterial related diseases. More particularly it relates to the treatment of bacterial infections and bacterial related diseases within the oral cavity and the sinus by use of a composition comprising a colony stimulating factor (CSF).

BACKGROUND OF THE INVENTION

Periodontal diseases are caused by bacteria and toxins in dental plaque, which is a sticky colourless film constantly forming on the surfaces of the teeth. These diseases are very common; it has been estimated that they affect as much as between 70-90% of the world population, and they are the major cause of tooth loss in people over 35 years of age.

There are many forms of periodontal disease. The most common ones include gingivitis, aggressive periodontitis and chronic periodontitis.

Gingivitis is the mildest form of periodontal disease, causing the gingiva to become red, swollen, and bleed easily. Gingivitis, if untreated, is thought to develop into periodontitis. In periodontitis the infection has progressed to involve the oral tissues which retain the teeth in the jawbone. If untreated, periodontitis ultimately leads to loss of the affected tooth.

Aggressive periodontitis may occur in patients who are otherwise clinically healthy. It is characterized i.e. by rapid attachment loss and bone destruction and familial aggregation. Clinically, chronic inflammation of gingiva, bleeding from periodontal pockets, alveolar bone resorption and the like are observed, and it is known that mobility and movement of teeth occur as the destruction advances, finally causing spontaneous loss of a tooth or a necessity of tooth extraction.

Chronic periodontitis, the most frequently occurring form of periodontitis, results in inflammation within the supporting tissues of the teeth, progressive loss of attachment as well as progressive alveolar bone resorption. This form of periodontitis is characterized by pocket formation and/or recession of the gingiva. As the destruction advances, the mobility and movement of teeth increase finally causing spontaneous loss of a tooth or a necessity of tooth extraction.

Non-surgical periodontal treatment includes scaling and root planing, optionally followed by adjunctive therapy such as local delivery of antimicrobials, mainly tetracycline antibiotics, with the aim of removing periodontitis-associated bacteria. However, periodontal disease is often quite refractile to treatment and discontinuation of therapy is often associated with the return of the potential pathogens to the pockets. Again, surgery or tooth extraction may be the final resort.

In order to overcome the problem with recurrence of bacterial infection, long-term antibacterial therapy has been used, but this form of treatment may give rise to development of resistant strains and super-imposed infections. Antibacterial agents such as chlorhexidine and quaternary ammonium salts in the form of mouth rinses also have been tried but these agents are unable to affect the subgingival flora when administered in liquid form as they do not penetrate into the pockets which are the result of the disease. Hence, they cannot be used in mouth rinses to treat an established periodontal disease.

The sinus are normally sterile air spaces found in the facial bones that surround the nose, including areas within the cheek bones and in the bones of the forehead above the eyes. Tooth and gum infections can spread to the sinus, and the infection is then called sinusitis. Sinusitis can be either acute (symptoms present for less than about 1 month), subacute (symptoms for about 1 to about 4 months), or chronic (symptoms for more than about 4 months).

Bacteria commonly involved in sinusitis are *Haemophilus influenzae* and *Streptococcus pneumoniae*. In chronic sinusitis a higher incidence of anaerobic organisms is seen (e.g. *Bacteroides, Peptostreptococcus*, and *Fusobacterium* species).

Symptoms of sinusitis include nasal congestion and plentiful, thick, coloured nasal drainage, bad-tasting post-nasal drip, cough, head congestion and an accompanying headache, a feeling of facial swelling, toothache, constant tiredness, and occasionally, a fever. The infection can spread to the facial bones or the membranes lining the brain (meningitis). Occasionally, sinusitis can spread to form a pocket of pus (abscess) in an eye socket, the brain or a facial bone.

Analgesics, such as e.g. paracetamol, help to relieve pain and lower temperature. Decongestants, such as pseudoephedrine, reduce the swelling in the nose and allow the sinus to drain. However, in general, prolonged use of decongestants can actually aggravate the nasal blockage. Also, antibiotic therapy may be used, but resistance may occur. As a last resort, endoscopic nasal surgery may be performed.

M. van Agtoven et al. (Rhinology, 40, 69-74, 2002), refer to clinical studies in non-neutropenic subjects that have indicated that Filgrastim (a recombinant granulocyte colony stimulating factor) may be beneficial as adjunctive therapy for treatment of serious bacterial and opportunistic fungal infections in non-neutropenic patients. The authors report the treatment of patients suffering from severe chronic bacterial sinusitis by administration of a combination of Ciprofloxacin 500-750 mg twice a day and Clindamycin 450-600 mg 3 times a day for 14 days, in combination with Filgrastim 300 μg subcutaneously (s.c.) (or placebo s.c.) once a day for the first 14 days and for another 10 weeks with either Filgrastim 300 μg s.c. or placebo s.c. on alternate days. In this case the total number of leukocytes is raised, thereby strengthening the immune defence.

Brent Weston et al (Journal of laboratory and clinical medicine 117(1991):4) and J. Goultchin at al in a case report (J. Periodontol. September 2000) describe the effect of treatment with G-CSF on dental status in a few patients with congenital neutropenia. They used i.v. injections of the substance to stimulate the bone marrow and could show some improvement of periodontitis and oral ulcers. This is expected because of the enhancement of the immune defence. Comparison with the majority of patients is difficult since patients with congential neutropenïa have disturbed dental development from early age.

Gamoual J. et al (J. Clin. Periodontology 2003; 30; 616-62) refer to studies with chronic periodontitis patients concerning apoptosis in neutrophils. Although the total amount of GM- CSF in samples from the gingiva in healthy subject and patients with periodontitis did not differ significantly, they suggest a novel mechanism by which neurophils accumulate in adult patients with peridontitis. As a result they found that GM-CSF reduces neutrophil apoptosis. They did not treat any patients or discuss this possibility.

CSF compositions have been clinically used for the treatment of myelo-suppression caused by chemotherapeutical or irradiation treatment of cancer. Other clinical uses of CSFs have also been suggested. Thus, WO 03/039444 discloses the use of various chemokines and cytokines, i.e. CSF, for the treatment of viral and/or fungal skin diseases. U.S. Pat. No. 6,689,351 discloses methods for promoting accelerated wound healing in patients suffering from a variety of wounds by topical administration of GM-CSF.

The chemical structure of CSFs has been studied and elucidated by means of techniques such as X ray crystallography and Nuclear Magnetic Resonance, see e.g. Hill, C. P., Osslund, T. D., Eisenberg, D. The structure of granulocyte-colony-stimulating factor and its relationship to other growth factors. Proc Natl Acad Sci U S A 90 pp. 5167 (1993) and Zink, T., Ross, A., Luers, K., Cieslar, C., Rudolph, R., Holak, T. A.: Structure and dynamics of the human granulocyte colony-stimulating factor determined by NMR spectroscopy. Loop mobility in a four-helix-bundle protein. Biochemistry 33 pp. 8453 (1994).

The most important aspect of the invention is the recalcification of the teeth after the rapid elimination of the infection and bacterial related disease. This is accomplished by a local treatment and not by stimulating the bone marrow as in the traditional way.

One conclusion drawn from the recalcification is that the same method could be used for treating fractures.

It appears that both bacterial sinusitis and periodontal disease are localized bacterial infections and bacterial related diseases that, albeit to different degrees, may be prone to becoming chronic and in the end may have to be treated by surgery. Obviously, in both diseases, there still is a need for an efficacious medicament permitting avoidance of both surgical measures and prolonged chemotherapeutical, e.g. antibiotic, treatment. Preferably, such medicament should be able to offer essentially total cure so as to diminish the probability of recurrence of the disease. In other words, it would be very advantageous if such a medicament would offer not only short-term but also long-term amelioration of the disease, such as the gingival and dental status of a subject suffering from any stadium of a periodontal disease, from gingivitis to severe periodontitis. In particular, a medicament permitting reversal of even advanced periodontitis without necessity of any surgical intervention would be extremely advantageous.

The primary object of the present invention is to provide such a medicament.

SUMMARY OF THE INVENTION

According to one aspect the present invention relates to the use of at least one colony stimulating factor (CSF) or fragment or derivative thereof having essentially the biological functionality and activity of the CSF for preparing a medicament for the treatment of a localized bacterial infection and bacterial related disease, and calcification of affected bone tissue.

According to another aspect the invention provides a composition for treatment of a localized bacterial infection and bacterial related disease comprising at least one CSF or fragment or derivative thereof.

According to still another-aspect the present invention relates to a method of treatment of a mammal suffering from a bacterial infection and bacterial related disease by administration of a therapeutically effective amount of a at least one CSF or fragment or derivative thereof having essentially the biological functionality and activity of the CSF. In this invention the use of CSF is different from the commonly used i.v. or s.c. route where the bone marrow is the target, i.e. to stimulate the production of macrophages and granulocytes.

The CSF may be a Granulocyte-Colony Stimulating Factor (G-CSF), Macrophage-Colony Stimulating Factor (M-CSF), Granulocyte-Macrophage-Colony Stimulating Factor (GM-CSF) or a multi-Colony Stimulating Factor (multi-CSF).

By the method of treatment of the invention, healing of a tooth affected by a periodontal disease is achieved in two steps, by
  1. eradication of the bacterial infection and bacterial related disease; and
  2. the tooth growing on to the bone (recalcification).

Further aspects and embodiments of the invention are as defined in the claims.

DETAILED DESCRIPTION OF THE INVENTION

The present invention is based on the surprising discovery that local administration of a therapeutically effective amount of at least one CSF is susceptible of providing a substantial improvement of a localized bacterial infection and bacterial related disease. Indeed, as described in an example herein below, by injection of only one dose of a GM-CSF preparation into the gingival tissue in the close vicinity of a tooth severely affected by periodontitis, and in fact scheduled for removal, the tooth was saved: the dental status quickly improved without recurrence of the disease.

On the other hand, it was noted that the injection of the GM-CSF had an effect not only on the dental status of the patient, but also on the chronic sinusitis from which the patient suffered. Indeed, subsequently to the injection the patient felt a marked decongesting effect on the sinus and experienced a substantial nasal outflow smelling of pus, followed by cure of the sinusitis.

The local treatment with CSF is mainly thought to act by activation and chemotaxis.

Without wishing to be bound to any theory, it is believed that the local administration of CSF stimulates the immune defence locally without causing any substantial systemic effect at the low dosage delivered, and that additionally, in the case of alveolar bone resorption in periodontitis, bone regeneration is locally stimulated.

It is a very advantageous feature of the present invention that localized bacterial infections and bacterial related diseases may be treated by local delivery of small doses of the inventive composition in a limited part of the body without any substantial systemic effect on the subject treated.

Consequently, the present invention relates to a medicament and a method for the treatment of a localized bacterial infection and bacterial related disease. The expression "Localized bacterial infection and bacterial related disease", as used herein refers to a bacterial infection and bacterial related disease that essentially afflict a limited area of the body of a mammal. Thus, whereas periodontal diseases and sinusitis are localized bacterial infections and bacterial related diseases, e.g. septicaemia is not.

Cytokines are regulatory proteins that are secreted by white blood cells and several other cell types in the body. Their pleiotropic actions include the regulation of innate and adaptive immune responses and the modulation of inflammatory responses. There are various kinds of cytokines, such as Interleukins, Interferon, Platelet-Activating Factor and Colony stimulating factors (CSFs). CSFs may be subdivided into Granulocyte-Colony Stimulating Factor (G-CSF), Macrophage-Colony stimulating factor (M-CSF), Granulocyte-Macrophage-Colony stimulating factor (GM-CSF) and multi-colony stimulating factor (multi-CSF, also referred to as Interleukin-3).

CSFs are required for survival, proliferation and differentiation of the myeloid progenitors committed to form mature neutrophil granulocytes, monocytes and mature macrophages that controls production of white blood cells. For example, G-CSF stimulates the production of predominantly neutrophil granulocytic colonies. M-CSF, on the other hand, acts solely on macrophage progenitors. M-CSF appears early in embryogenesis, suggesting a potential developmental role for this polypeptide. GM-CSF controls the irreversible commitment of macrophage and granulocytic progenitor cells. Although GM-CSF acts on the same progenitor cell lineage as G-CSF, it also stimulates the production of monocytes.

GM-CSF also has a considerable effect on the function of mature myeloid cells, including enhanced antibody production, phagocytosis and cytotoxicity. At lower concentrations, such as those achieved according to the present invention, this activation of the myeloid cells is largely a local effect.

CSFs may be prepared e.g. by recombinant techniques (rCSFs), well known to the person skilled in the art. As an example, the production of recombinant GM-CSF (rGM-CSF) by culturing a host cell transformed with a vector comprising a gene coding for a primate GM-CSF protein is disclosed in European Patent No. 0 188 479. Procedures for the production of recombinant human GM-CSF have also been described by Burgess et al. [(1987) Blood, vol. 69, No. 1: 43-51]. The production of recombinant G-CSF (rG-CSF) has been described in U.S. Pat. No. 4,810,643.

CSFs also are commercially available. As an example, Molgramostim, an rGM-CSF, is sold by Schering-Plough under the trade name Leucomax®. Another rGM-CSF is Sargramostirn, sold by Schering AG in Germany under the trade name Leukine®. Filgrastim, is an rG-CSF is commercialized by Amgen under the Neupogen® and Granulokine® trade names.

Any CSFs analogs or derivatives endowed with comparable or enhanced in vivo biological activity can be used in accordance with the present invention. CSF analogs may be generated by the deletion, insertion, or substitution of amino acids in the primary structure of the naturally occurring glycoproteins, or by chemical modification of the glycoprotein.

The CSF preferably is administered in a pharmaceutical formulation or composition comprising a therapeutically effective amount thereof in association with one or more pharmaceutically acceptable carriers and/or adjuvants. The carriers employed must be compatible with all the ingredients in the formulation. Any formulation method include the step of bringing the biologically active ingredient into association with the carrier(s) and/or adjuvant(s), such as by dissolving or suspending the CSF in a liquid or semi-liquid vehicle or carrier phase.

Formulations suitable for local administration in accordance with the present invention comprise therapeutically effective amounts of the therapeutic agent with one or more pharmaceutically acceptable carriers and/or adjuvants. An aqueous carrier is preferred.

For example, the CSF formulation may be provided as a sterile, injectable solution in a vial. It also may be provided as a lyophilized sterile powder to be reconstituted with sterile or bacteriostatic water for injection.

It also is contemplated that the pharmaceutical composition of the invention comprises an admixture of more than one type of CSF, e.g. GM-CSF in combination with G-CSF and/or M-CSF. Such admixture may formulated and administered essentially in the same way as a composition comprising only one CSF as an active ingredient.

For general information on pharmaceutical formulations and methods of preparing pharmaceutical formulations reference may be made to Remington: The Science and Practice of Pharmacy, 19th ed., Mack Printing Company, Easton, Pa. (1995).

The formulations of the invention are locally administered in the nose and/or mouth of a mammal, preferably a human, by a method permitting passage through the mucosal linings thereof. When for treatment of a periodontal disease, an injection preferably is made in proximity of the afflicted area, e.g. in or beside the periodontal crevice. Injection administration may be performed by topical injection into periodontal tissues around alveolar bone, namely into gingiva, alveolar mucosa, sublingual mucosa, palate part and the like. The "alveolar mucosa injection method" as discussed in U.S. Pat. No. 6,682,718 may suitably be used. In this method, a drug solution is injected between periosteum of the alveolar bone and alveolar mucosa by inserting a needle not vertically but in a laying position into a flexible oral mucosa region adjacent to gingiva.

The inventive formulations also may be administered in the nose and/or mouth by spraying. The frequency of administration may range from once daily to several times per day.

The CSF formulation for topical injection may contain aseptic aqueous or non-aqueous solutions, as well as suspending agents or emulsifying agents. Examples of the aqueous solutions include distilled water for injection and physiological saline. The formulation may further contain auxiliary agents such as an antiseptic agent, a moistening agent, an emulsifying agent, a dispersing agent, a stabilizing agent, a solubilization-assisting agent and an isotonicity agent. Sterilization of the formulation may be effected by filtration through a bacteria-retaining filter, adding a germicide or by irradiation. The formulation may be produced under aseptic condition or by firstly producing aseptic solid compositions and then dissolving in sterile water or a sterile solvent for injection prior to use.

Administration also may be performed by use of a gel, or by any other pharmaceutical carrier of similar rheological character, e.g. comprising a slow release formulation, to be applied directly in the gingival or periodontal crevice, or an implantable device delivering a suitable amount of the CSF at a suitable rate. Implantable devices for use in the treatment of a periodontal disease are described e.g. in U.S. Pat. No. 5,023, 082. Slow release formulations of GM-CSF are disclosed in U.S. Pat. No. 6,274,175.

For the treatment of sinusitis, injection of the CSF formulation preferably is made in the palate, but the CSF formulation also may be administered by spraying into the nostrils or by inhalation.

The CSF dosage administered may range from 5 to 800 µg per administration, more preferably from 20 to 400 µg per administration, most preferably from 50 to 100 per administration. Administration may be performed at a frequency ranging from daily administration to administration once every third week, e.g. from once to three times a week. The total duration of the treatment may range from one single administration occasion to a period of three weeks. The physician in charge will be able to determine suitable dosage size, as well as the frequency and duration of the administration.

A therapeutically effective amount of at least one other active ingredient may also be administered to the treated subject. Such active ingredient is selected in view of the particular condition to be treated. E.g. the composition may comprise an antibacterial agent effective against the bacteria involved in the disease. When for example the disease is periodontitis, involving mostly anaerobic bacteria, a suitable antibacterial compound may be the antibiotic metronidazol. This antibiotic may be administered incorporated in the same formulation as the CSF or in a separate formulation, such as the dental gel Elyzol®. However, of course, other antibiotics may be used equally well.

Still other active ingredients may be e.g. a phosphate ion releasing preparation and/or a combination of calcium and vitamin D3. For example, 0.5 to 2 g calcium and 20 to 100 µg vitamin D3 may be given during the treatment period, or during a period to be determined by the clinician in charge.

Still other active ingredients may be selected from magnesium, fluor and vitamin C and D, as well as combinations thereof or with any of the above-mentioned other active ingredients, e.g. calcium.

In the treatment of sinusitis, an antibiotic, a decongestant or a steroidal compound also may be administered either separately from the CSF or in the same formulation. An example of a suitable decongestant formulation is Rinexin®, an example of a suitable steroidal formulation is Nasonex® spray.

In the manufacturing of a medicament according to the invention a lyophilized CSF preparation may be used. For example the preparation may be dissolved ex tempore in a suitable liquid carrier. If not intended for immediate use, the liquid formulation of the CSF may be preserved in a refrigerator or freezer or else the shelf life may be improved by addition of a suitable preservative as well known to the person skilled in the art. An example of a suitable preservative would be benzyl alcohol, added e.g. at a concentration of 1-2% by weight of the formulation to an aqueous solution of a CSF.

Also, a two chamber syringe with a lyophilized CSF preparation and a suitable liquid carrier may be uses which would allow storage at room temperature.

Another way would be to use one-dose elastic vials of gel, equipped with a small needle for application in the pockets surrounding the affected tooth.

In the presently preferred embodiment of the invention the CSF is GM-CSF and the medicament is for administration as a liquid injection preparation containing a dosage of 50-100 µg in a liquid volume of 0.05 to 0.2 ml.

The following examples are offered to more fully illustrate the present invention, but are not intended to limit the scope thereof.

EXAMPLES

| Formulation for injection | |
|---|---|
| GM-CSF (Molgramostim) | 50 µg |
| Water for injection qs | 100 µl |

Molgramostim was dissolved in water for injection by gentle stirring at room temperature.

Treatment of Periodontitis

Example 1

A male patient, aged 47, suffered from severe periodontitis. One upper tooth in particular was considered irretrievable by the dentist in charge and extraction was scheduled. The patient was given one injection of 80 µg GM-CSF in the proximity of the periodontal crevice, once a week for three consecutive weeks. The periodontal infection and bacterial related disease were abolished and the attachment of the tooth to the jawbone was regained.

This patient also suffered from a chronic sinusitis. After having received the GM-CSF injection the patient experienced a marked improvement of the sinusitis and complete cure of the sinusitis was experienced at the term of the treatment period. Three years later the man was still free from periodontitis.

Example 2

A female patient, aged 59, suffered from severe periodontitis. Radiography of the teeth was made and showed deep periodontal crevices around several teeth. The patient was given one injection of 50 µg GM-CSF in the proximity of the periodontal crevices. The patient experienced a marked improvement. A second dental radiography was effected three months after the injection and of the same set of teeth. The marked improvement of the dental status was easily observed—the deep periodontal crevices have disappeared.

One year later no recurrence has occurred.

The invention claimed is:

1. A method for treating a mammal suffering from a periodontal disease, comprising locally administering by injection in the proximity of the periodontal disease a therapeutically effective amount of a therapeutic agent, said therapeutic agent consisting of one or more granulocyte-macrophage-colony stimulating factor (GM-CSF) polypeptides.

2. The method of claim 1, wherein the periodontal disease is gingivitis or periodontitis.

3. The method of claim 1, wherein the therapeutic agent is administered by injection through the mucosal lining of the gingiva or by application in a periodontal pocket.

4. The method of claim 1, wherein said GM-CSF is present in the therapeutic agent in a unit dosage amount of 5 µg to 800 µg.

5. The method of claim 4, wherein the unit dosage amount is 50 µg to 100 µg.

6. The method of claim 1, wherein the therapeutic agent is administered at intervals ranging from once a day to once every third week.

7. The method of claim 1, wherein the therapeutic agent is administered a total of 1 to 3 times for a period of one week.

8. The method of claim 1, wherein the therapeutic agent is administered by injection into the alveolar mucosa.

9. The method of claim 1, wherein the therapeutic agent is administered by injection into the sublingual mucosa.

10. The method of claim 1, wherein the therapeutic agent is administered by injection between the periosteum of the alveolar bone and the alveolar mucosa, and wherein a needle used for injection is inserted into a flexible oral mucosal region adjacent to the gingiva.

11. The method of claim 1, wherein the mammal is a human.

* * * * *